(12) United States Patent
Piantoni et al.

(10) Patent No.: US 10,166,698 B2
(45) Date of Patent: Jan. 1, 2019

(54) CRUSHING MILL FOR CRUSHING FIBROUS MATERIAL AND A UNIT FOR FORMING ABSORBENT CORES IN A MACHINE WHICH MAKES ABSORBENT SANITARY ARTICLES

(71) Applicant: GDM S.p.A., Bologna (IT)

(72) Inventors: Matteo Piantoni, Albino (IT); Valerio Soli, Bologna (IT)

(73) Assignee: GDM S.P.A., Bologna (IT)

( * ) Notice: Subject to any disclaimer, the term of this patent is extended or adjusted under 35 U.S.C. 154(b) by 0 days.

(21) Appl. No.: 15/556,796

(22) PCT Filed: Mar. 15, 2016

(86) PCT No.: PCT/IB2016/051456
§ 371 (c)(1),
(2) Date: Sep. 8, 2017

(87) PCT Pub. No.: WO2016/147113
PCT Pub. Date: Sep. 22, 2016

(65) Prior Publication Data
US 2018/0043576 A1    Feb. 15, 2018

(30) Foreign Application Priority Data

Mar. 19, 2015  (IT) .............................. BO2015A0136

(51) Int. Cl.
*B29B 7/60*     (2006.01)
*A61F 13/15*   (2006.01)
*B02C 18/14*   (2006.01)
*B02C 18/22*   (2006.01)
(Continued)

(52) U.S. Cl.
CPC .......... *B29B 7/60* (2013.01); *A61F 13/15617* (2013.01); *A61F 13/15658* (2013.01);
(Continued)

(58) Field of Classification Search
CPC ........ B29L 2031/4878; A61F 13/15617; A61F 13/15707; A61F 13/15764;
(Continued)

(56) References Cited

U.S. PATENT DOCUMENTS 4,610,678 A * 9/1986 Weisman .......... A61F 13/15203
                                                604/368
4,773,903 A * 9/1988 Weisman .......... A61F 13/15203
                                                604/368
(Continued)

FOREIGN PATENT DOCUMENTS

EP   0453892 A1   10/1991
EP   1666010 A1   6/2006

OTHER PUBLICATIONS

International Search Report dated Jun. 6, 2016 for counterpart PCT Application No. PCT/IB2016/051456.

*Primary Examiner* — James P Mackey
(74) *Attorney, Agent, or Firm* — Shuttleworth & Ingersoll, PLC; Timothy Klima

(57) ABSTRACT

A crushing mill for crushing fibrous material for a unit for forming absorbent cores in a machine which makes absorbent sanitary articles, including a casing having an infeed opening and an outfeed opening for the fibrous material, a rotor rotatable about its axis of rotation and housed in the casing at an intermediate position between the infeed opening and the outfeed opening. Also provided is an auxiliary opening operatively interposed between the infeed opening and the outfeed opening, with reference to a direction of rotation of the rotor, and adapted to allow feeding a particulate absorbent material into an intermediate zone between the infeed opening and the outfeed opening.

20 Claims, 5 Drawing Sheets

(51) Int. Cl.
  *B29B 7/34* (2006.01)
  *B29C 41/04* (2006.01)
  *B29B 7/40* (2006.01)
  *D21B 1/06* (2006.01)
  *B29K 105/12* (2006.01)
  *B29L 31/48* (2006.01)

(52) U.S. Cl.
  CPC .. *A61F 13/15707* (2013.01); *A61F 13/15764* (2013.01); *B02C 18/14* (2013.01); *B02C 18/2225* (2013.01); *B29B 7/34* (2013.01); *B29C 41/04* (2013.01); *B29B 7/401* (2013.01); *B29K 2105/12* (2013.01); *B29L 2031/4878* (2013.01); *D21B 1/068* (2013.01)

(58) Field of Classification Search
  CPC ........... A61F 2013/15943; B02C 18/14; B02C 18/148; B02C 18/2225; D04H 1/72; D04H 1/732; D21B 1/066; D21B 1/068; B29B 7/34; B29B 7/401; B29B 7/60
  See application file for complete search history.

(56) References Cited

U.S. PATENT DOCUMENTS

| | | | | |
|---|---|---|---|---|
| 5,350,624 | A * | 9/1994 | Georger | D04H 1/56 139/420 B |
| 5,750,066 | A * | 5/1998 | Vonderhaar | A61F 13/15658 264/510 |
| 6,982,052 | B2 * | 1/2006 | Daniels | A61F 13/15203 264/101 |
| 2006/0105075 | A1 * | 5/2006 | Otsubo | A61F 13/15626 425/363 |
| 2009/0270823 | A1 | 10/2009 | Meizelman | |
| 2009/0281511 | A1 * | 11/2009 | Fukae | A61F 13/15626 604/358 |
| 2013/0014899 | A1 * | 1/2013 | Nakano | A61F 13/15642 156/361 |
| 2014/0027943 | A1 * | 1/2014 | Hoshika | A61F 13/15658 264/121 |

* cited by examiner

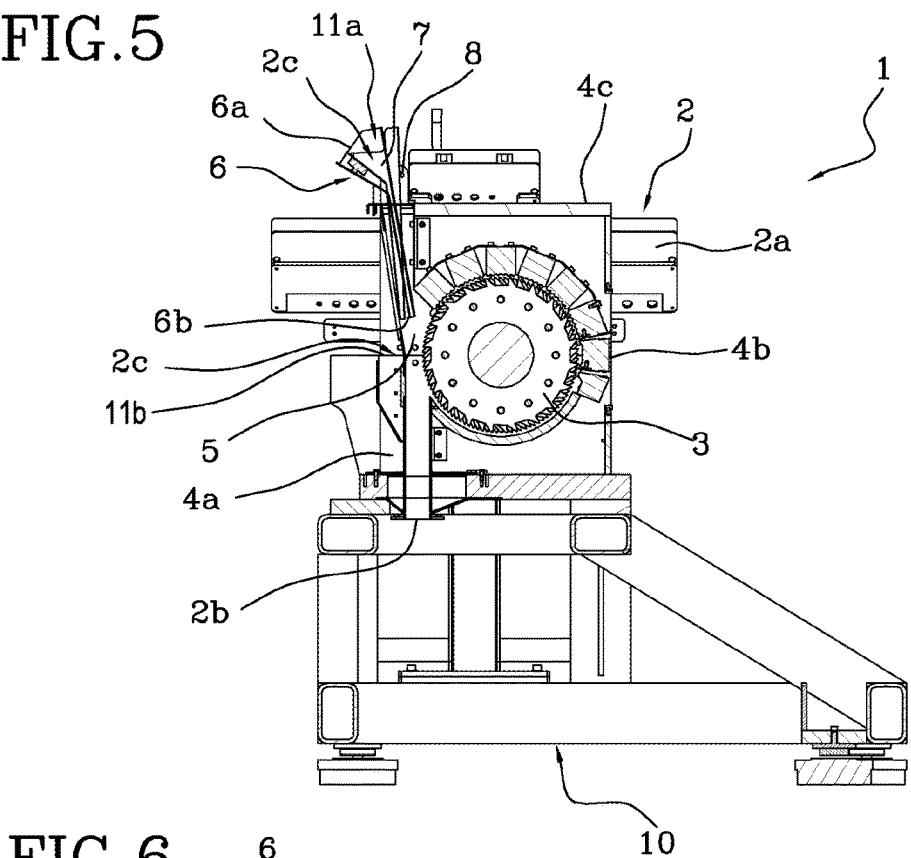
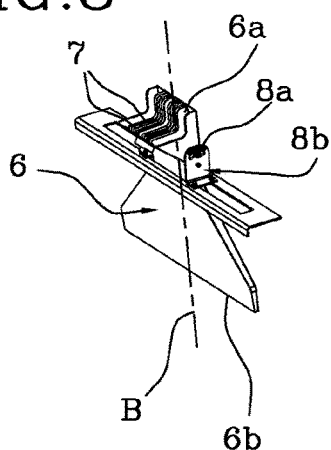
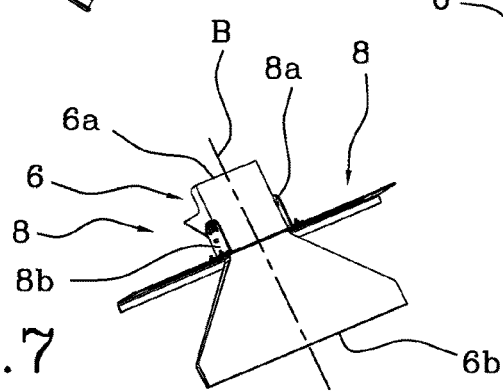

CRUSHING MILL FOR CRUSHING FIBROUS MATERIAL AND A UNIT FOR FORMING ABSORBENT CORES IN A MACHINE WHICH MAKES ABSORBENT SANITARY ARTICLES

This application is the National Phase of International Application PCT/IB2016/051456 filed Mar. 15, 2016 which designated the U.S.

This application claims priority to Italian Patent Application No. BO2015A000136 filed Mar. 19, 2015, which application is incorporated by reference herein.

TECHNICAL FIELD

This invention relates to a crushing mill for crushing fibrous material and to a unit for forming absorbent cores in a machine which makes absorbent sanitary articles.

BACKGROUND ART

More specifically, this invention applies to the manufacture of sanitary underwear such as baby nappies, sanitary towels or the like.

As is known, nappies comprise an absorbent core or pad which is normally enclosed between a permeable inner layer of non-woven fabric and an impermeable outer layer of polyethylene.

Absorbent pads of known type comprise an absorbent core made of an absorbent material, such as, for example, granules of superabsorbent polymer material (SAP) inside a mixture of containment cellulose pulp (fluff) and absorbent material binder, sandwiched between two layers of non-woven fabric.

In particular, core forming units known in the prior art comprise a station for feeding the fibrous material, or fluff, and a station for supplying the superabsorbent polymer material, the two stations being mounted in parallel and combined at a forming duct or chamber.

More specifically, prior art units comprise a mill for crushing the fibrous material, provided with one or more inlets through which the fibrous material in the form of a web or chain of fibres is fed in, and a crushing rotor in which the material is broken up as much as possible into individual fibres which are subsequently allowed to drop through an outfeed opening.

Downstream of the outfeed opening there is a forming duct which is generally provided with nozzles that deliver granules of superabsorbent polymer material which are scattered into the duct and embedded in the fluff fibres.

Disadvantageously, the scattering of the particles of superabsorbent polymer material inside the duct is often of low quality, in particular with reference to products of the latest generation, where the quantity of superabsorbent polymer material tends more and more to exceed that of the other absorbent material.

DISCLOSURE OF THE INVENTION

The aim of this invention is therefore to provide a crushing mill for crushing fibrous material and a unit for forming absorbent cores in a machine which makes absorbent sanitary articles to overcome the above mentioned disadvantages of the prior art.

More precisely, the aim of this invention is to provide a crushing mill for crushing fibrous material and capable of distributing the superabsorbent polymer material in the fibrous material in maximized and uniform manner.

Another aim of the invention is to provide a high performing crushing mill for crushing fibrous material and able to be integrated in pre-existing units for forming absorbent cores.

More specifically, this invention has for an aim to provide a unit for forming the absorbent cores in a machine for making absorbent sanitary articles and capable of making absorbent sanitary articles of high quality.

These aims are achieved by a crushing mill for crushing fibrous material and having the features disclosed herein, as well as by a unit having features disclosed herein, for forming the absorbent cores in a machine for making absorbent sanitary articles.

More specifically, the proposed aims are achieved by a crushing mill for crushing fibrous material for a unit for forming absorbent cores in a machine which makes absorbent sanitary articles, comprising a casing having an infeed opening and an outfeed opening for the fibrous material, a rotor rotatable about its axis of rotation and housed in the casing at an intermediate position between the infeed opening and the outfeed opening.

According to the invention, the mill comprises at least one auxiliary opening operatively interposed between the infeed opening and the outfeed opening, with reference to a direction of rotation of the rotor, and adapted to allow feeding a particulate absorbent material into an intermediate zone between the infeed opening and the outfeed opening.

Advantageously, that way, the point of intersection between the superabsorbent polymer material and the fibrous material is located inside the casing, allowing the two materials to be mixed completely inside the forming chamber or duct which, being rectilinear (because the two axes of rotation are at right angles to each other), prevents blockages.

Preferably, the mill comprises a diffuser member located at the auxiliary opening of the casing and extending along a direction of extension between an infeed portion of it for feeding in, and an outfeed portion of it for feeding out, the particulate absorbent material, the width of the infeed portion, measured at right angles to the direction of extension being smaller than the corresponding width of the outfeed portion.

Advantageously, that way, the mill according to the invention may also be retrofitted in a forming unit of prior art type, where the means for feeding the polymer material are typically provided with a conveyor belt of limited width.

Further, the diffuser member is preferably connected to the casing by connecting means which are adjustable so that their position or orientation inside the auxiliary opening can be varied.

Advantageously, the operator can thus adapt the inclination or position of the diffuser member to suit the type of particulate material, the flow quantity thereof and the working conditions of the unit.

BRIEF DESCRIPTION OF THE DRAWINGS

These and other features will become more apparent from the following description of a preferred, and hence non-exclusive and non-limiting example embodiment of a crushing mill for crushing fibrous material and of a unit for forming the absorbent cores In a machine for making absorbent sanitary articles according to this invention, with reference to the accompanying drawings in which:

FIG. 5 shows the mill in a cross section cut along the line V-V in FIG. 3;

FIGS. 6-8 show three perspective views of a detail of the mill of FIGS. 3 and 4.

DETAILED DESCRIPTION OF PREFERRED EMBODIMENTS OF THE INVENTION

Figure 1:
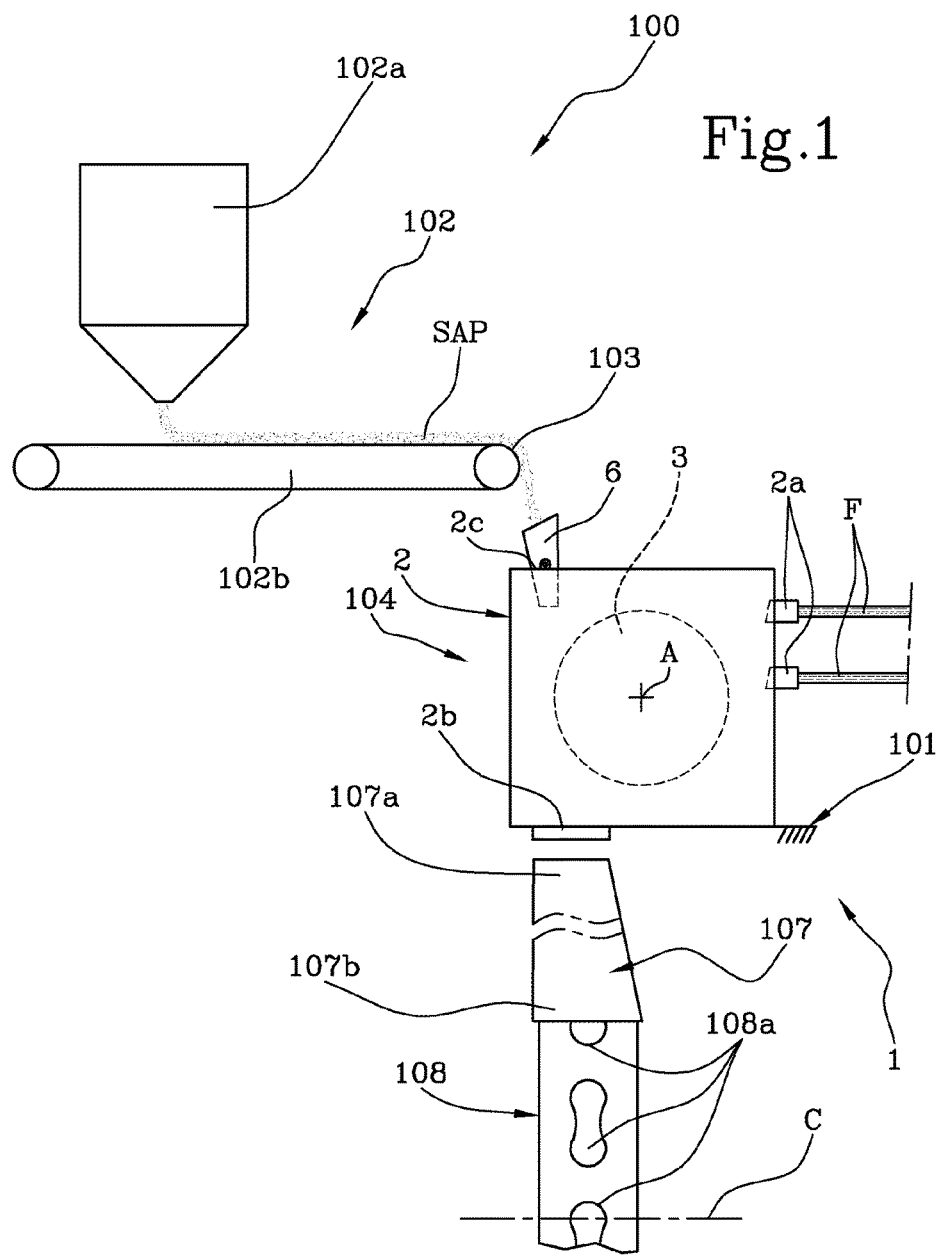
FIGS. 1 and 2 show two schematic, side and front views of a unit according to this invention for forming the absorbent cores in a machine for making absorbent sanitary articles.
Figure 2:
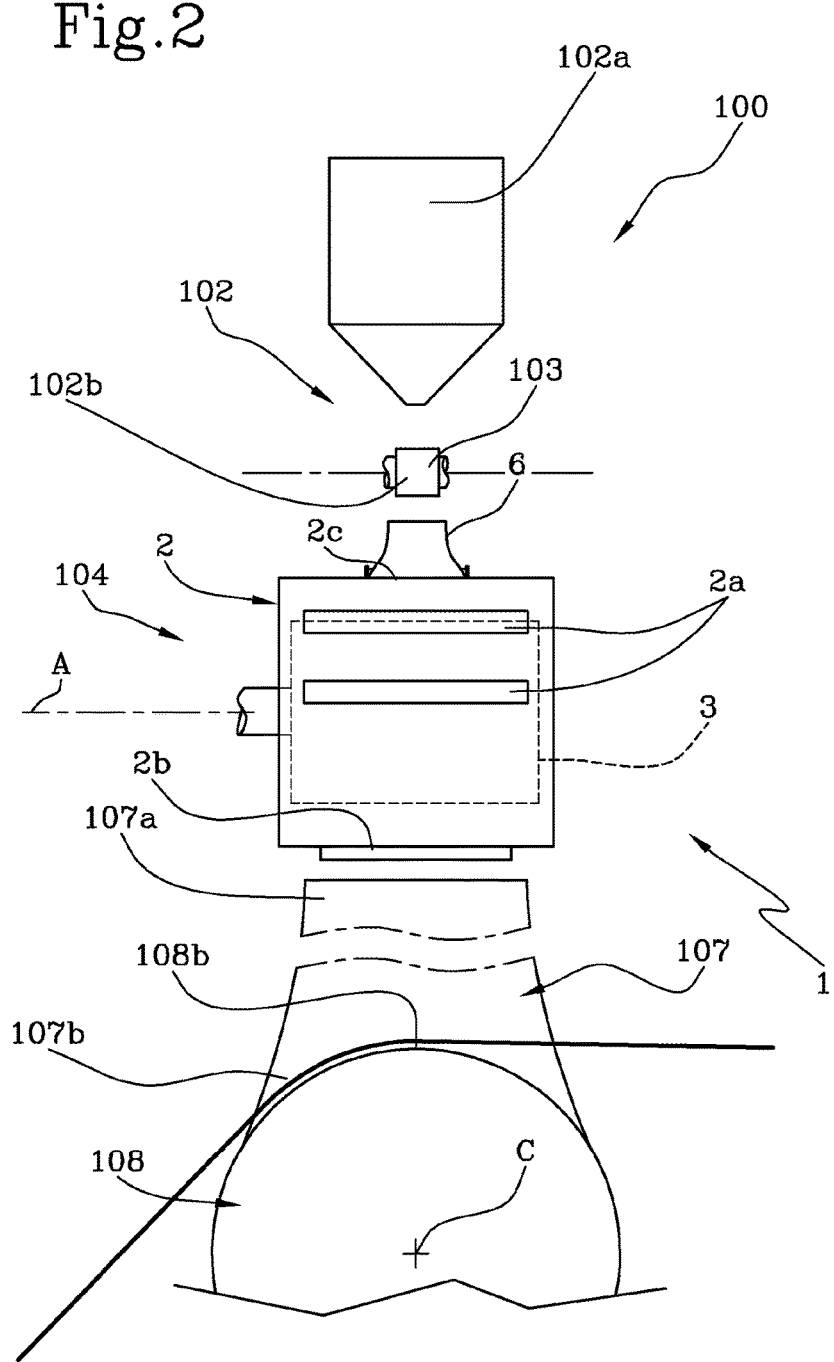
Figure 3:
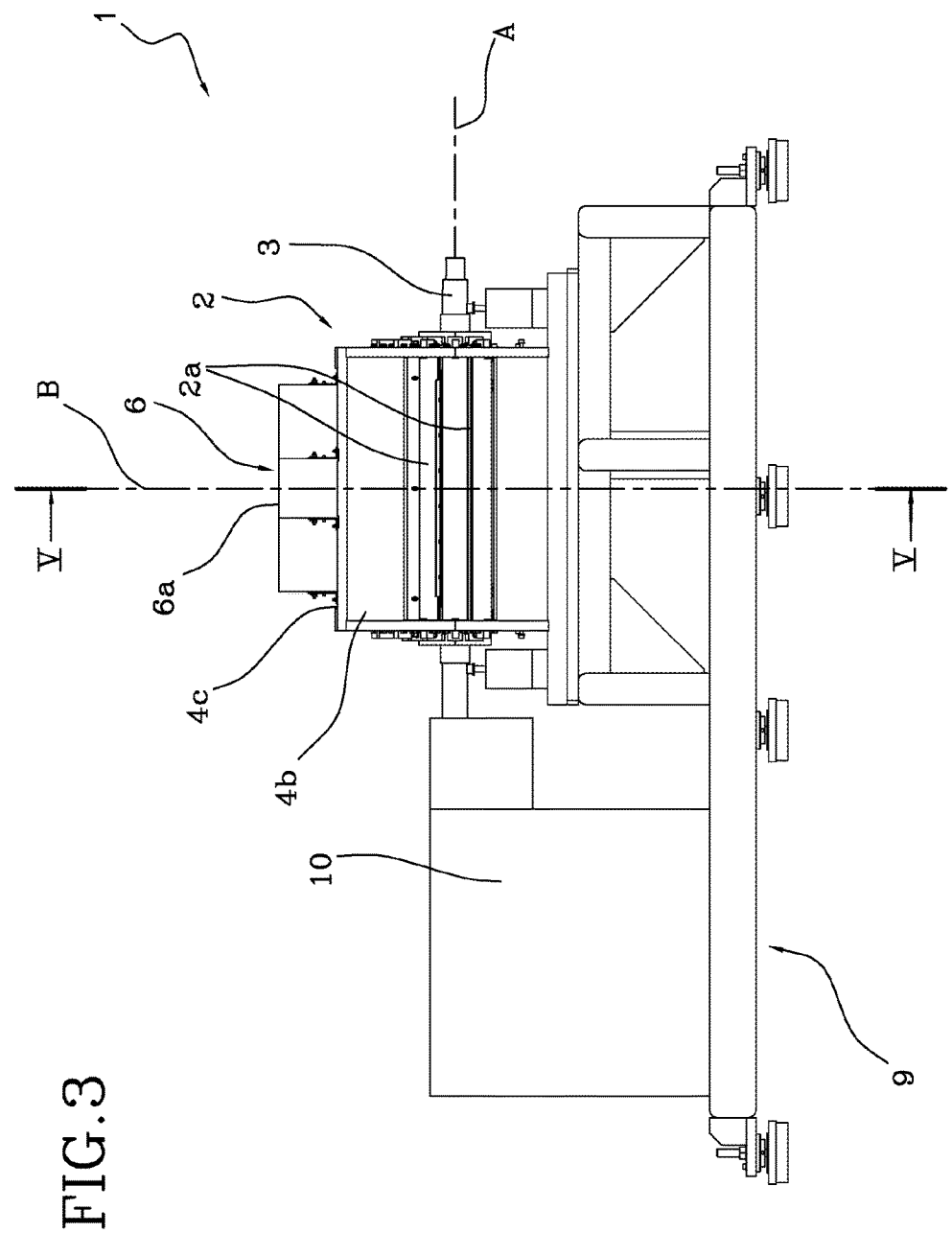
FIGS. 3 and 4 show a front view and a plan view of a crushing mill for crushing fibrous material according to this invention.
Figure 4:
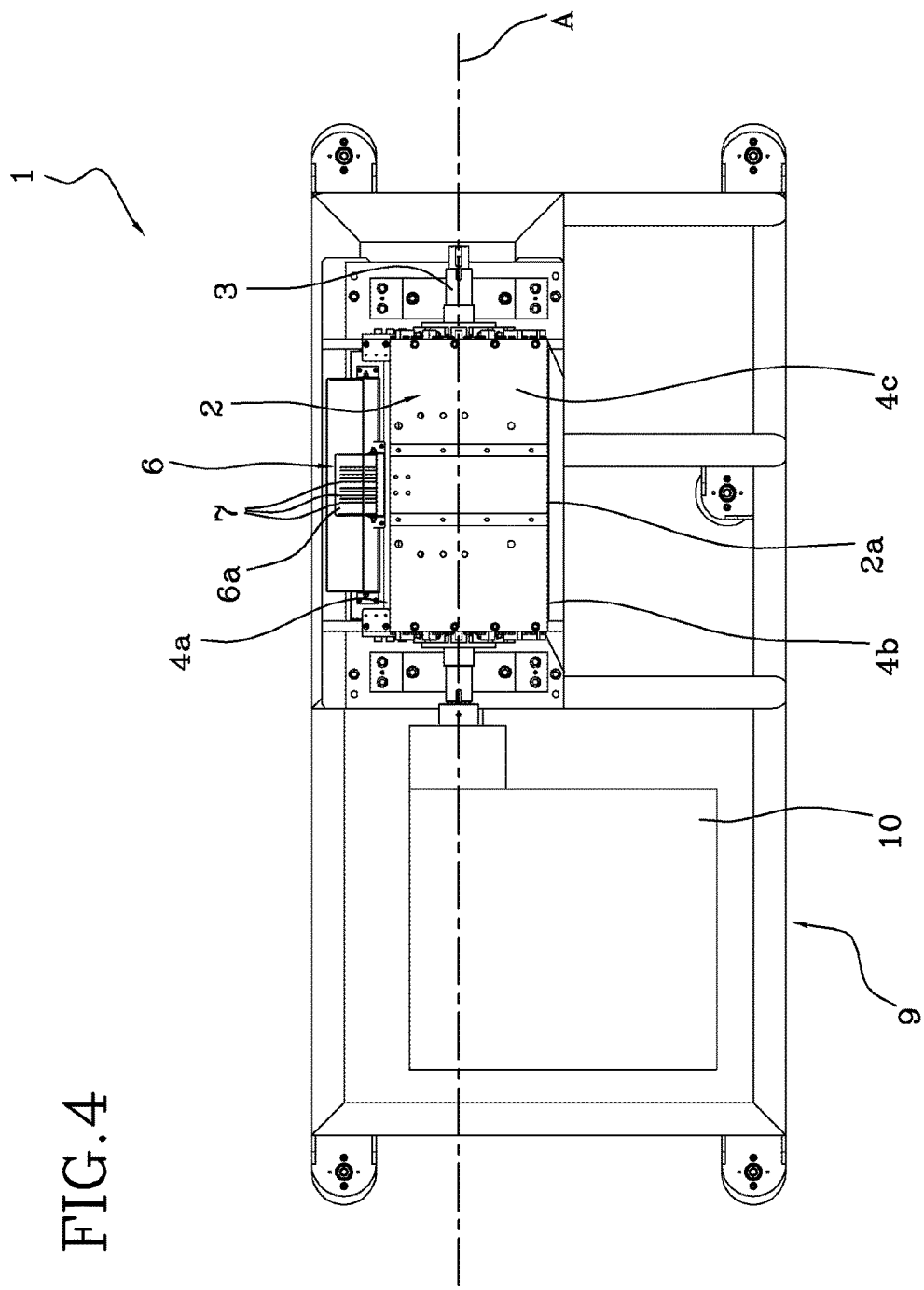

With reference to the accompanying drawings, the numeral 1 denotes a crushing mill for crushing fibrous material according to this invention, to be used preferably in a forming unit 100 for forming the absorbent cores in a machine which makes absorbent sanitary articles.

The forming unit 100 is designed to be installed in a machine for making absorbent sanitary articles such as, for example, baby and adult nappies, that is to say, articles having an absorbent core comprising both a portion of fibrous material (fluff) and a portion of superabsorbent particulate material (SAP).

The expression "fibrous material" is used in this text to denote a material defined by elongate, filamentous fibres, such as cellulose pulp, for example.

The expression "superabsorbent particulate material" is used in this text to denote a loose material, generally in granular form, having a very high absorption capacity.

The unit 100 for forming the core thus comprises feeding means 101 for feeding the fibrous material "F" and feeding means 102 for feeding the particulate absorbent material "SAP".

The feeding means 101 for feeding the fibrous material preferably comprise at least one roller for unwinding a roll of fibrous material and feeding means for feeding the roll along a movement direction.

The feeding means 102 for feeding the particulate absorbent material "SAP", on the other hand, comprise a storage tank 102a and a distribution unit 102b configured to withdraw or receive the material from the tank 102a and to move it translationally, with a preset feed front of predetermined size, away from the tank 102a.

Preferably, the distribution unit 102b comprises at least one transfer element 103 designed to move a predetermined flow quantity "0" of particulate absorbent material "SAP" away from the tank 102a with a feed front having a predetermined width.

Preferably, the transfer element 103 is defined by a conveyor belt.

In some embodiments, the transfer element 103 is defined by a vibrating member (not illustrated) used to widen the feed front of the particulate material "SAP" between an infeed section of it and an outfeed section of it.

The forming unit 100 also comprises crushing means 104 configured to crush the fibrous material "F" by separating the fibres from each other in such a way as to produce of flow of loose material.

The crushing means 104 comprise a mill 1 according to this invention.

The mill 1 comprises at least one casing 2 having an infeed opening 2a and an outfeed opening 2b for the fibrous material "F" and a rotor 3 (or grinder) rotatable about its axis of rotation "A" and housed inside the casing 2.

To set the rotor 3 in rotation, there is a motor 10, or drive, coupled to the rotor 3 itself.

It should be noted that the casing 2, and preferably the motor 10, are anchored to a base 9 which allows positioning the mill.

The infeed opening 2a is associated with, or facing, the feeding means 101 to receive the fibrous material "F" which is then fed and crushed in the mill 1 by means of the rotor 3 and then released through the outfeed opening 2b.

Thus, with reference to a direction of movement of the fibrous material "F" inside the casing 2, the rotor 3 is located at an intermediate position between the infeed opening 2a and the outfeed opening 2b.

According to one aspect of the invention, the feeding means 102 for feeding the particulate absorbent material "SAP" are configured to deliver this material into the casing 2, in an intermediate zone between the infeed opening 2a and the outfeed opening 2b.

In this regard, the casing 2 comprises at least one auxiliary opening 2c operatively interposed between the infeed opening 2a and the outfeed opening 2b, with reference to a direction of rotation of the rotor 3, and adapted to allow feeding the particulate absorbent material "SAP" into an intermediate zone between the infeed opening 2a and the outfeed opening 2b.

Thus, the auxiliary opening 2c is associated with the feeding means 102 for feeding the particulate absorbent material "SAP".

Preferably, the rotor 3 is located at a level above the outfeed opening 2b so as to facilitate feeding out the ground (or crushed) fibrous material "F" by gravity, that is, letting it drop out. In this regard, it should be noted that the auxiliary opening 2c faces the rotor 3.

More precisely, the auxiliary opening 2c is located at a height above the outfeed opening 2b in order to allow the particulate absorbent material "SAP" to flow out by gravity.

The outfeed opening 2b is located at a height lower than both the auxiliary opening 2c and the rotor 3 so as to allow the crushed fibrous material "F" and the particulate absorbent material "SAP" to flow out by gravity simultaneously.

Preferably, the casing 2 of the mill 1 has at least a first wall 4a facing the rotor 3 and placed at a predetermined distance therefrom to form a discharge channel 5 through which the fibrous material "F" (and the particulate material "SAP") can flow out and which leads to the outfeed opening 2b.

More precisely, the casing 2 of the mill 1 has at least a first wall 4a and a second wall 4b, which are both substantially parallel to the axis of rotation "A" and between which the rotor 3 is interposed.

The auxiliary opening 2c and the infeed opening 2a are made close to the first wall 4a and to the second wall 4b, respectively.

In the preferred embodiment, the casing 2 is a box-shaped body having a plurality of walls, including the first wall 4a, the second wall 4b and a top wall 4c joining them.

Preferably, the auxiliary opening 2c is made in the first wall 4a or in the top wall 4c, in the proximity of a zone joining the walls 4a, 4c.

Preferably, also, in order to maximize flexibility of use, the casing 2 has two auxiliary openings 2c, one proximal to 11b, and one distal from 11a, the outfeed opening 2b.

Thus, advantageously, the point where the crushed fibrous material "F" and the particulate absorbent material "SAP" are mixed can be moved freely by the operator to a greater or smaller height as a function of the operating parameters of the forming unit 100, such as, for example, materials, flow quantity, size of depositing zone, etc.

The auxiliary openings 2c are therefore alternately connected, or connectable, to the feeding means 102 for feeding the particulate absorbent material "SAP", preferably defining two alternative options for setting up the forming unit 100.

Preferably, the auxiliary opening 2c (or the auxiliary openings 2c) has a main direction of extension which is substantially parallel to the axis of rotation "A" of the rotor 3.

To facilitate placing the mill 1 in prior art forming units, there is a diffuser member 6 associated with the mill 1 at the auxiliary opening 2c of the casing 2.

The diffuser member 6 is configured to widen the feed front of the particulate absorbent material "SAP" arriving from the feeding means 102, thus facilitating its scattering in the casing 2.

Preferably, the diffuser member 6 extends along a direction of extension "B" between an infeed portion 6a of it for feeding in, and an outfeed portion 6b of it for feeding out, the particulate absorbent material "SAP".

It should be noted that to allow distribution, that is to say, to allow widening the feed front, the width of the infeed portion 6a, measured at right angles to the direction of extension "B", is smaller than the corresponding width of the outfeed portion 6b.

The infeed portion 6a is located in a release zone of the feeding means 102, preferably at an end portion of the transfer element 103.

More preferably, the diffuser member 6 comprises a plurality of channels 7, each extending with increasing width, from the infeed portion 6a to the outfeed portion 6b.

Advantageously, that way, the particles (or granules) of particulate material inside the adjoining channels 7 are guided away from each other, thus widening the feed front and facilitating scattering of the particulate absorbent material "SAP" inside the mill 1.

Preferably, the channels are separated from each other by longitudinal partitions which are spaced in such a way as to produce in each zone a predetermined density of the particulate absorbent material "SAP".

More precisely, in a preferred embodiment, these partitions are movable towards and away from each other transversely to the direction of extension "B" in order to vary the flow quantity of particulate absorbent material "SAP" and/or to modulate its density in each zone (centre or periphery of the core).

In the embodiment illustrated, the diffuser member 6 is connected to the casing 2 and positioned so it passes through the auxiliary opening 2c in such a way that the infeed portion 6a is outside the casing 2 and the outfeed portion 6b is inside the casing 2.

In accordance with the foregoing, the outfeed portion 6b of the diffuser member 6 is preferably located inside the casing 2 and faces the rotor 3 of the mill 1.

More specifically, in a first configuration (illustrated), where the diffuser member 6 is associated with the distal auxiliary opening, the outfeed portion 6b of the diffuser member 6 is located at a height above the axis of rotation "A" of the rotor 3.

Alternatively, in a second configuration (not illustrated), where the diffuser member 6 is associated with the proximal auxiliary opening, the outfeed portion 6b of the diffuser member 6 is located at a height below the axis of rotation "A" of the rotor 3.

In the preferred embodiment, the diffuser member 6 is preferably connected to the casing 2 by connecting means 8 which are adjustable so that their position or orientation inside the auxiliary opening 2c can be varied.

Thus, advantageously, the operator can vary the relative position (or orientation) of the diffuser member 6 relative to the casing 2, modifying the parabola followed by the particulate absorbent material "SAP" as it falls.

In other words, by varying the position of the diffuser member, the operator can modify the point where the particulate absorbent material "SAP" mixes with the fibrous material "F", thus modifying the mixing process as a function of parameters such, for example:

flow quantity of the particulate absorbent material "SAP";
flow quantity of the fibrous material "F";
size and weight of the granules;
size of the absorbent cores to be made;
speed of rotation and feed of the belts;
etc.

In effect, it should be noted that the further the mixing point is from the mill 1, the more the distribution of the particulate material "SAP" is concentrated in a central zone, and vice versa.

Preferably, the adjustable connecting means 8 comprise at least a pin 8a about which the diffuser member 6 is rotatable in order to vary its orientation.

Also provided is at least one locking or clamping unit 8b adapted to lock the diffuser member 6 at the desired angular position It should be noted that the pin 8a is preferably parallel to the axis of rotation of the rotor 3.

Located operatively downstream of the mill 1 there is a mixing duct 107 (or chamber).

In the duct 107, the crushed fibrous material "F" feeding out of the mill and the particulate absorbent material "SAP" are mixed together.

The mixing duct 107 (or chamber) is thus located operatively downstream of the outfeed opening 2b of the casing 2 and extends away from the mill 1.

More precisely, the duct extends between an inlet 107a, butted against and connected to the outfeed opening 2b of the casing 2 and an outlet 107b, located away from the inlet 107a at a forming drum 108 (described better below).

Preferably, therefore, the duct 107 extends in a direction which is mainly vertical (substantially vertical).

Thus, the inlet 107a is located at a height above the outlet 107b.

It should be noted that the duct 107 extends in a substantially linear direction and is preferably flared from the inlet 107a towards the outlet 107b in order to facilitate mixing the products and preventing blockages.

For this purpose, the forming unit 100 comprises the aforementioned drum 108 for forming an absorbent core.

This drum is rotatable about its central axis "C" and is provided, along its periphery, with a plurality of recesses 108a for receiving the material released by the duct 107.

Thus, the periphery of the forming drum 108, in a material receiving zone 108b, is butted against the outlet 107b of the duct 107.

The recesses 108a are preferably suction tiles provided with vacuum generating means (of essentially known type) by which they hold the material in position.

In the preferred embodiment, the vacuum generating means are sized to produce a suction effect on the crushed fibrous material "F" and on the particulate absorbent material "SAP" feeding out of the mill 1.

In other words, the vacuum generated in the recesses 108a by the vacuum generating means is such as to produce a suction effect at the outfeed opening 2b of the casing 2.

Consequently, the simultaneous outflow of the crushed fibrous material "F" and of the particulate absorbent material "SAP" into the duct 107 occurs thanks to the action of gravity combined with that of the vacuum generating means, thus guaranteeing greater transit speed and better placement precision.

According to one aspect of the invention, the axis of rotation "A" of the rotor 3 of the mill 1 is transverse (preferably at right angles) to the central axis "C" of the forming drum 108.

Advantageously, that way, the feed direction of the fibrous material "F" and of the particulate material "SAP" is the same as the feed direction of the tiles, no twisting or rotation of the duct 107 being necessary.

The invention achieves the preset aims and brings important advantages.

In effect, the presence of an auxiliary opening in the mill to allow the particulate material to be fed into the casing optimizes mixing the two absorbent materials.

More specifically, gravity feeding the particulate absorbent material in the same direction as the fibrous material facilitates mixing the two materials, making it possible to obtain a highly homogeneous product.

Furthermore, the presence of a diffuser member capable of widening the feed front of the particulate material allows use of a mill according to this invention even in a prior art forming unit as a simple substitute or retrofit part Moreover, the fact that the axis of rotation of the drum and that of the mill rotor are at right angles allows maximizing the transit of the particulate and crushed materials, preventing blockages.

The invention claimed is:

1. A forming unit for forming absorbent cores for a machine which makes absorbent sanitary articles, comprising:
    a crushing device for receiving and crushing a fibrous material;
    a particulate absorbent material feeding unit for feeding a particulate absorbent material into the crushing device, the particulate absorbent material feeding unit including a storage tank and a distribution unit including a surface for feeding the particulate absorbent material;
    a mixing duct in which the crushed fibrous material and the particulate absorbent material are mixed to form a mixed material and which is operatively located downstream of the crushing device and extends away from the crushing device;
    a forming drum by which the absorbent cores of the absorbent sanitary articles are formed, the forming drum being rotatable about a central axis thereof and including, along a periphery thereof, a plurality of recesses for receiving the mixed material released by the mixing duct;
    wherein the crushing device includes a crushing mill, comprising:
        a casing including an infeed opening and an outfeed opening for the fibrous material;
        a rotor rotatable about an axis of rotation thereof and housed in the casing at an intermediate position between the infeed opening and the outfeed opening;
        an auxiliary opening operatively interposed between the infeed opening and the outfeed opening, with reference to a direction of rotation of the rotor, and adapted to allow feeding the particulate absorbent material into an intermediate zone between the infeed opening and the outfeed opening;
        wherein the axis of rotation of the rotor is transversal to the central axis of the forming drum and the particulate absorbent material feeding unit is associated with the auxiliary opening to release the particulate absorbent material into the casing.

2. The forming unit according to claim 1, wherein the crushing mill comprises a diffuser member, the diffuser member including an infeed portion for feeding in the particulate absorbent material and an outfeed portion for feeding out the particulate absorbent material, the diffuser member being located at the auxiliary opening of the casing and extending along a direction of extension between the infeed portion, and the outfeed portion, wherein a width of the infeed portion, measured at right angles to the direction of extension is smaller than a corresponding width of the outfeed portion.

3. The forming unit according to claim 2, wherein the diffuser member comprises a plurality of channels, each extending, with increasing width, from the infeed portion to the outfeed portion.

4. The forming unit according to claim 2, wherein the diffuser member is connected to the casing and positioned so the diffuser member passes through the auxiliary opening such that the infeed portion is outside the casing and the outfeed portion is inside the casing.

5. The forming unit according to claim 2, wherein the outfeed portion of the diffuser member is located inside the casing and faces the rotor.

6. The forming unit according to claim 2, and further comprising an adjustable connecting device by which at least one chosen from a position and an orientation of the diffuser member inside the auxiliary opening is variable, and wherein the diffuser member is connected to the casing by the adjustable connecting device.

7. The forming unit according to claim 6, wherein the adjustable connecting device comprises a pin about which the diffuser member is rotatable in order to vary the orientation of the diffuser member, and at least one locking or clamping unit adapted to lock the diffuser member at a desired angular position.

8. The forming unit according to claim 1, wherein the auxiliary opening faces the rotor and has a main direction of extension which is parallel to the axis of rotation of the rotor.

9. The forming unit according to claim 1, wherein the casing includes a first wall and a second wall between which the rotor is interposed, the first wall and the second wall being parallel to the axis of rotation; the first wall being located at a preset distance from the rotor to form a discharge channel through which the fibrous material is fed out and which leads to the outfeed opening; the auxiliary opening being made through the first wall and the infeed opening being made through the second wall.

10. The forming unit according to claim 9, wherein, in use, the outfeed opening is located at a height lower than the auxiliary opening to allow the crushed fibrous material and the particulate absorbent material to flow out by gravity.

11. The forming unit according to claim 1, wherein the casing has two auxiliary openings, one proximal to, and one distal from, the outfeed opening.

12. The forming unit according to claim 2, wherein the diffuser member is configured to widen a feed front of the particulate absorbent material to facilitate dispersion of the particulate absorbent material in the fibrous material.

13. The forming unit according to claim 2, wherein the particulate absorbent material feeding unit comprises a transfer element configured to move a predetermined flow quantity of particulate absorbent material towards the auxiliary opening along a feeding direction and with a feed front of predetermined width.

14. A crushing mill for crushing fibrous material for a unit for forming absorbent cores in a machine which makes absorbent sanitary articles, comprising:

a casing including an infeed opening and an outfeed opening for fibrous material;

a rotor rotatable about an axis of rotation thereof and housed in the casing at an intermediate position between the infeed opening and the outfeed opening;

an auxiliary opening operatively interposed between the infeed opening and the outfeed opening, with reference to a direction of rotation of the rotor, and adapted to allow feeding particulate absorbent material into an intermediate zone between the infeed opening and the outfeed opening;

a diffuser member, the diffuser member including an infeed portion for feeding in the particulate absorbent material and an outfeed portion for feeding out the particulate absorbent material, the diffuser member being located at the auxiliary opening of the casing and extending along a direction of extension between the infeed portion and the outfeed portion, wherein a width of the infeed portion, measured at right angles to the direction of extension is smaller than a corresponding width of the outfeed portion.

15. The crushing mill according to claim 14, wherein the diffuser member comprises a plurality of channels, each extending, with increasing width, from the infeed portion to the outfeed portion.

16. The crushing mill according to claim 14, wherein the diffuser member is connected to the casing and positioned so the diffuser member passes through the auxiliary opening such that the infeed portion is outside the casing and the outfeed portion is inside the casing.

17. The crushing mill according to claim 14, wherein the outfeed portion of the diffuser member is located inside the casing and faces the rotor.

18. The crushing mill according to claim 14, and further comprising an adjustable connecting device by which at least one chosen from a position and an orientation of the diffuser member inside the auxiliary opening is variable, and wherein the diffuser member is connected to the casing by the adjustable connecting device.

19. The crushing mill according to claim 18, wherein the adjustable connecting device comprises a pin about which the diffuser member is rotatable in order to vary the orientation of the diffuser member, and at least one locking or clamping unit adapted to lock the diffuser member at a desired angular position.

20. The crushing mill according to claim 14, wherein the auxiliary opening faces the rotor and has a main direction of extension which is parallel to the axis of rotation of the rotor.

* * * * *